(12) United States Patent
Lagace

(10) Patent No.: US 6,542,240 B2
(45) Date of Patent: Apr. 1, 2003

(54) METHOD OF IDENTIFYING DEFECTIVE ROLL ON A STRIP PROCESSING LINE

(75) Inventor: Helene P. Lagace, Kingston (CA)

(73) Assignee: Alcan International Limited, Montreal (CA)

( * ) Notice: Subject to any disclaimer, the term of this patent is extended or adjusted under 35 U.S.C. 154(b) by 21 days.

(21) Appl. No.: 09/823,555

(22) Filed: Mar. 30, 2001

(65) Prior Publication Data

US 2002/0176083 A1 Nov. 28, 2002

(51) Int. Cl.$^7$ .......................... B21B 37/08; G01N 21/89
(52) U.S. Cl. ................... 356/429; 356/430; 250/559.01
(58) Field of Search .................. 356/429, 430; 250/559.01, 559.07, 559.08, 559.4, 559.42, 559.46

(56) References Cited

U.S. PATENT DOCUMENTS

| | | | | |
|---|---|---|---|---|
| 3,795,124 A | * | 3/1974 | Diolot ...................... | 72/13.3 |
| 3,812,373 A | * | 5/1974 | Hosoe et al. ........... | 250/559.39 |
| 4,507,564 A | * | 3/1985 | Shimada ................ | 250/559.06 |
| 4,709,157 A | * | 11/1987 | Shimizu et al. ........ | 250/559.46 |
| 4,958,307 A | * | 9/1990 | Nishimura ............. | 250/559.08 |

FOREIGN PATENT DOCUMENTS

| | | |
|---|---|---|
| DE | 293 068 A5 | 10/1983 |
| DE | 19812353 | 10/1999 |
| JP | 4-224017 | 8/1992 |

OTHER PUBLICATIONS

International Search Report dated Jul. 23, 2002 in PCT/CA02/00403 (European Patent Office).
Patent Abstracts of Japan, vol. 016, No. 576 (M–1345), Dec. 16, 1992, abstract of JP 04 224017A.
Patent Abstracts of Japan, vol. 005, No. 151 (M–089), Sep. 24, 1981, abstract of JP 56 080321A.

\* cited by examiner

Primary Examiner—John R. Lee
Assistant Examiner—Anthony Quash
(74) Attorney, Agent, or Firm—Cooper & Dunham LLP

(57) ABSTRACT

A defective roll in a strip processing line, e.g. an aluminum alloy strip cleaning line, may create an undesirable mark on the strip material. Where a plurality of rolls are in use, the defective roll is identified by providing a downstream inspection station which includes a data processor. When a mark on the strip passes the inspection station, the processor is activated whereby the rolls go through a timed opening and closing sequence. During this sequence, if no mark is observed on the strip at the time when a repeat of the mark would be expected, the lapsed time is compared to a data base and the defective roll is thereby identified.

8 Claims, 2 Drawing Sheets

METHOD OF IDENTIFYING DEFECTIVE ROLL ON A STRIP PROCESSING LINE

BACKGROUND OF THE INVENTION

This invention relates to a method of identifying the location of a defective roll in a strip processing line where a defective roll causes a visible repeating mark on the material being processed.

In the processing of strip material, e.g. aluminum alloy strip, it is commonplace to pass the strip material between rolls. For instance, during cleaning of aluminum alloy strip, the strip may be passed through cleaning tanks or enclosures where the rolls are hidden from view. In such a situation, a defective roll within the tank may be causing a visible repeating pattern mark on the strip material emerging from the tank. It becomes a very difficult matter to determine which one of the rolls within the tank is in fact the one causing the visible repeating pattern mark on the strip material.

At present, the only way of identifying a defective roll is to either shut down and disassemble the line in order to inspect each roll individually for damage or by lifting rolls from the sheet one by one until the defective roll is identified.

In German Democratic Republic Patent DD 293 068 a defective roll is located by a series of calculations that also involve a factor representing the amount of length extension the strip undergoes as its thickness is being reduced by a rolling process.

There remains a need for a convenient system for detecting defective rolls in a strip processing line, e.g. squeegee rolls found inside the tanks of a strip cleaning operation.

SUMMARY OF THE INVENTION

The present invention in its broadest aspect relates to a method of identifying the location of a defective roll in a strip processing line wherein a defective roll causes a visible repeating mark on the material being processed. The strip processing line includes a plurality of laterally spaced pairs of rolls between which the strip material is carried and means for opening and closing the roll pairs. An inspection station is provided downstream of the plurality of rolls to inspect for visible marks or defects on the strip emerging from the rolls and data processing means are provided for selectively opening and closing roll pairs in timed sequence. Actuating means are also provided at the inspection station for actuating the data processing means. In accordance with the method of the invention, when a mark or defect on the strip material passes the inspection station, the data processing means is actuated thereby starting the timed opening of the rolls. When the absence of a mark is detected at the inspection station the timed sequence is stopped. Since the mark appears once with each revolution of a roll, the marks will appear equally spaced along the strip, e.g. at equal time intervals. Thus, the absence of a mark at the expected location (time interval) means that the defective roll was out of contact with the strip at that time. The lapsed time between the timed opening and the detection of the absence of a mark is recorded and compared against a data base indicating the location of a roll relative to the lapsed time thereby identifying the defective roll.

The method is generally used with rolls of equal diameter but may also be used where the rolls have different diameters. Thus, the spacing between the marks on the strip indicates the circumference of the rolls. By having the rolls identified in the data processor according to their circumference (or diameter), when the absence of a mark is recorded, the spacing on the strip is also recorded and relates to the circumference in the memory thereby identifying the defective roll. Also, the roll pairs may be opened individually or in groups. In a situation where two adjacent roll pairs are spaced at a distance along the strip less than the circumference of the rolls, these adjacent roll pairs must open separately from each other in order to separately detect each roll pair by lapsed time. For instance, they may open as parts of two separate groups of rolls that open together.

The operating system relies on time measurements to locate the defective roll. Therefore, if the time interval between the closing of a first roll and the opening of a second roll is set to the time it takes a point on the sheet surface to move a distance of at least one full roll circumference, then the system is able to detect the single roll that is causing the defect.

In a preferred embodiment, when a visible repeating mark or defect is noted on the strip material, an operator goes to an inspection station at the downstream end of the processing tank or enclosure. The inspection station includes a marker adjacent the strip material and a data processing unit which includes an activating push button and a signal light. In order to conduct a test, the operator first slows down the line to an inspection speed, e.g. about 10 mpm. When a mark or defect on the strip material is observed to pass the marker, the push button is immediately activated. This sets in motion a timed sequence measured from the first roll pair at the entry to the processing tank or enclosure. The data processor calculates the time required for a point on the strip to move from the entry point to the marker of the inspection station and provides a signal when that time has lapsed. If at that point in time a mark or defect does not pass the indicator, then the operator immediately pushes the button to end the test. The time is recorded and compared against a data base and a screen at the inspection station indicates which roll pair has caused the mark or defect.

It is also possible to fully automate the procedure to detect the defective roll. Instead of an operator at the inspection station, a scanning system, e.g. a computerized camera system, may be used which is adapted to detect a mark or defect on the strip material. Thus, to conduct a search for a defective roll, the system is activated and when the scanner detects a mark or defect passing the inspection station the timed sequence is started as described above. Then, within a narrow time range within which the mark or defect should again appear, the scanner is again activated. If no mark or defect is detected within that narrow time range, the time is recorded and compared against a data base in the processor and the defective roll is identified.

DESCRIPTION OF THE PREFERRED EMBODIMENTS

Figure 1:
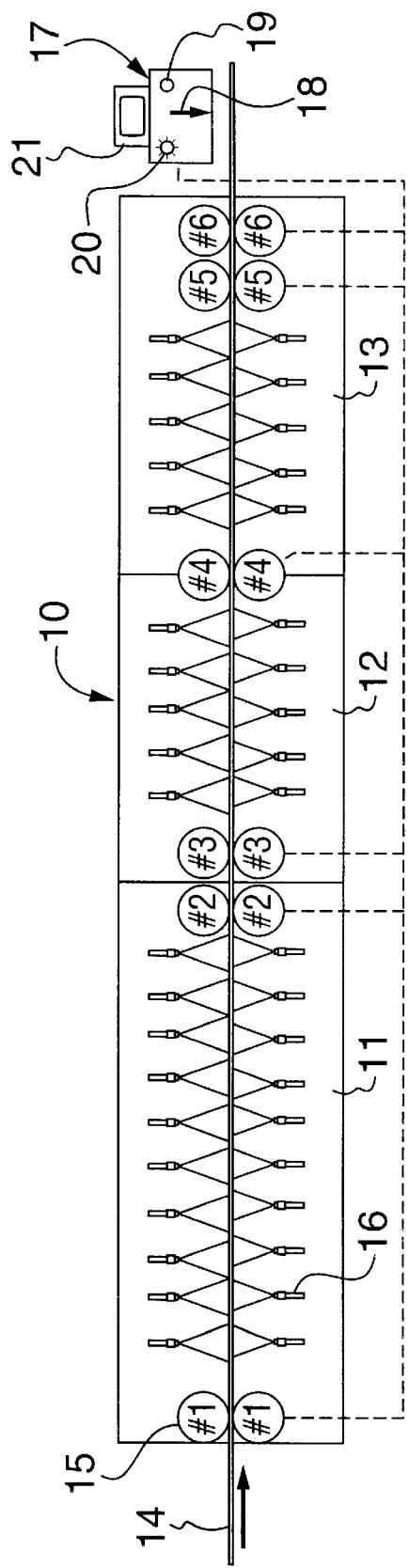
FIG. 1 is a schematic side elevation view of a strip cleaning tank incorporating the invention.
Figure 2:
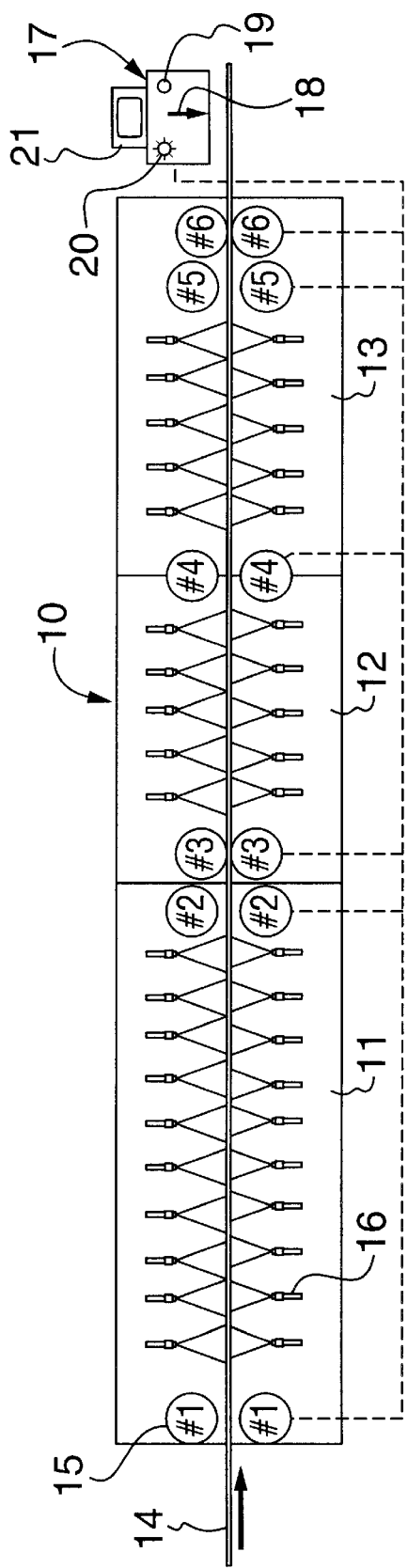
FIG. 2 is the same view as in FIG. 1 with a group of rolls in open position.

As shown in FIGS. 1 and 2, a strip cleaning tank 10 includes a cleaning section 11, a first rinse section 12 and a second rinse section 13. An aluminum alloy strip material 14 to be cleaned is passed through the cleaning line 10. The strip 14 passes through pairs of squeegee rolls 15 with the locations of these roll pairs being indicated by the numerals 1, 2, 3, 4, 5 and 6. Thus, in this embodiment roll pair 1 are located at the entry to the cleaning section 11. Roll pairs 2 and 3 are placed close together (less than a circumference apart) to form a seal between the cleaning section 11 and the first rinse section 12. Roll pair 4 are located between the two rinse sections 12 and 13. Roll pairs 5 and 6 are placed close together (less than one circumference apart) to form a seal at the exit from the second rinse section 13. The cleaning and rinsing is carried out by means of spray nozzles 16 positioned above and below the strip 14.

An inspection station 17 is positioned downstream of the cleaning tank 10 and includes a visual marker 18 located close to the strip 14. The station also includes a push button 19 for actuating the system and a pilot light 20. Also included is a screen 21 for displaying information and results.

For operation of the system, the inspection point 18 is located a fixed known distance from an upstream reference point, which typically the roll pair 1. In an example, the inspection point 18 is located 19.5 meters from roll pair 1. In this particular embodiment the measured distance from each roll to the inspection point is as shown in Table 1:

TABLE 1

| ROLL # | DISTANCE TO INSPECTION POINT |
|---|---|
| 1 | 17635 mm |
| 2 | 13215 mm |
| 3 | 12555 mm |
| 4 | 9555 mm |
| 5 | 6555 mm |
| 6 | 5955 mm |

Each roll has a circumference of approximately 960 mm so that marks on the strip from a defective roll will be approximately 960 mm apart. Since roll pairs 2 and 3 and roll pairs 5 and 6 are less than 960 mm apart, those rolls must be separately opened in order to locate a defective roll. For maximum efficiency in a test, the system can be arranged so that roll pairs 1, 2, 4 and 5 open as one group and roll pairs 3 and 6 open as a separate group. The arrangement with roll pairs 1, 2, 4 and 5 open is shown in FIG. 2.

The operational sequence is as follows:
(a) the operator selects an inspection speed, e.g. about 11 mpm, and the line decelerates;
(b) when a defect on the strip passes inspection point 18 the operator immediately presses button 19 thereby activating the processor, including timer T;
(c) at T=2 seconds, the pilot light 20 flashes (½ second on, ½ second off) and roll pairs 1, 2, 4 and 5 open;
(d) at T=8 seconds, roll pairs 1, 2, 4 and 5 close;
(e) at T=14 seconds, roll pairs 3 and 6 open;
(f) at T=20 seconds roll pairs 3 and 6 close and the pilot light shows a steady "ON";
(g) the operator now looks for an absence of a mark and when an absence is detected button 19 is pushed again (with this arrangement marks are expected every 960 mm or within a lapsed time of just over 5 second); and
(h) the pilot light 20 goes out and the value of T is measured.

The processor now compares the value of the measured T to the following Table 2.

TABLE 2

| ROLL | CALCULATED TIME BEFORE ABSENCE OF MARK (seconds) | RANGE (seconds) | MESSAGE AT SCREEN (21) |
|---|---|---|---|
| 1 | 98 | 95–101 | Test complete - INSPECT ROLL 1 |
| 2 | 74 | 71–77 | Test complete - INSPECT ROLL 2 |
| 3 | 82 | 79–85 | Test complete - INSPECT ROLL 3 |
| 4 | 54 | 51–57 | Test complete - INSPECT ROLL 4 |
| 5 | 38 | 35–41 | Test complete - INSPECT ROLL 5 |
| 6 | 46 | 43–49 | Test complete - INSPECT ROLL 6 |

If the operator does not press the button within two minutes or if the value of T1 is inconclusive, the following message is displayed: "Test complete—Results Inconclusive".

The pilot light goes out when the operator pushes the button or after two minutes has elapsed.

As an example from the above Table 2, roll pair 4 is 9555 mm from the inspection point 18. The strip 14 travels at an inspection speed of 11 mpm, i.e. 183 mm/sec. The distance of 9555 mm÷183 mm/sec.+a delay of 2 seconds results in a time of 54 seconds which identifies the defective roll as being at roll pair 4.

Figure 3:
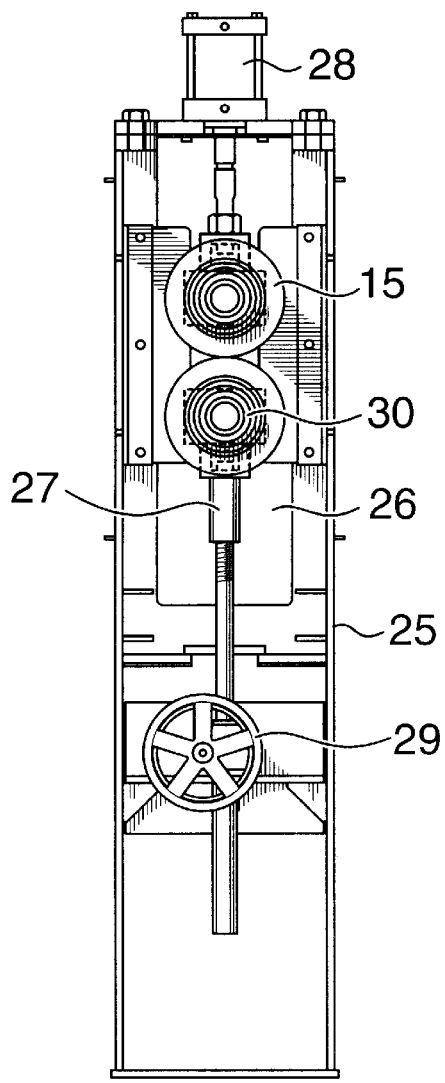
FIG. 3 is a side elevation of an opening and closing mechanism for a pair of rolls in closed position.
Figure 4:
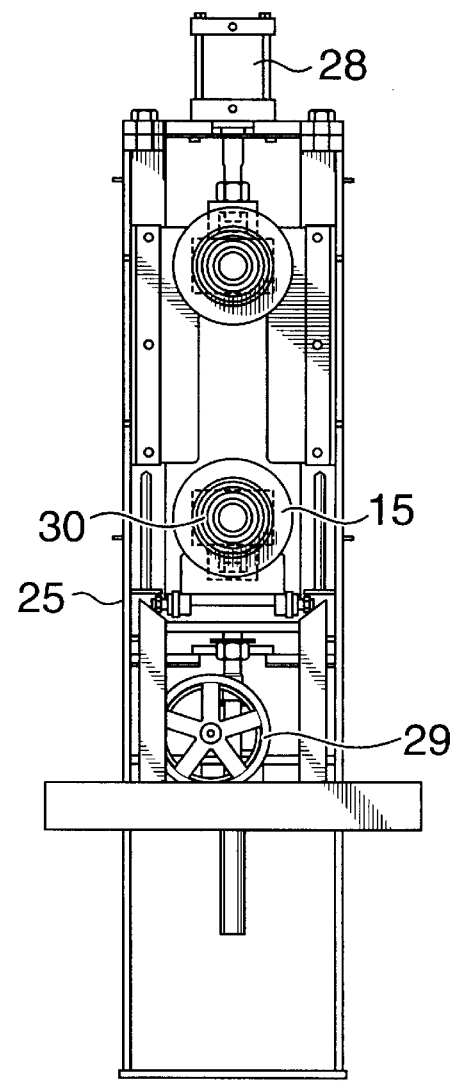
FIG. 4 is the same view as in FIG. 3 with a pair of rolls in open position.

An example of one suitable mechanism for opening and closing the roll pairs is shown in FIGS. 3 and 4. This is a pneumatic system 25 having a support plate 26 with an elongated slot 27 within which roll bearing assemblies 30 travel up and down. Pneumatic actuators 28 and 29 control the upper and lower rolls respectively, either applying a constant pressure as shown in FIG. 3 or opening the rolls as shown in FIG. 4 for testing.

It will, of course, be understood that any other suitable mechanism may be used that can either open the rolls or close them and apply constant pressure as described above.

What is claimed is:

1. A method of identifying the location of a defective roll in a strip processing line wherein a defective roll causes a visible repeating mark on the material being processed, said strip processing line including a plurality of laterally spaced pairs of rolls between which the strip material is carried, means for opening and closing roll pairs, an inspection station downstream of the rolls to inspect for visible marks on the strip emerging from the rolls, data processing means for selectively opening and closing pairs of rolls in timed sequence, and actuating means associated with the inspection station for actuating the data processing means, said method comprising actuating the data processing means when a mark on the strip material passes the inspection station thereby starting the timed opening and closing of said roll pairs in one or more groups in such that all roll pairs in each group are laterally spaced along the strip at a distance greater than the circumference of a roll and stopping the timed opening when the absence of a mark is detected at the inspection station, recording the lapsed time between the timed opening and the detection of the absence of a mark, and comparing the lapsed time to a data base indicating the location of a roll relative to the lapsed time thereby identifying the defective roll.

2. A method according to claim 1 wherein at least two of the roll pairs are laterally spaced along the strip at a distance less than the circumference of a roll.

3. A method according to claim 1 wherein at least two roll pairs are of equal diameter.

4. A method according to claim 1 wherein the rolls are all of equal diameter.

5. A method according to claim 1 wherein at least some of the rolls have different diameters.

6. A method according to claim 1 wherein the strip material is aluminum alloy sheet material.

7. A method according to claim 5 wherein the rolls are squeegee rolls operated inside a processing tank during a strip cleaning operation.

8. A method according to claim 1 wherein the inspection station is a visual station and an operator upon observing marks on the strip, slows down the line to test speed, actuates the data processing means as a mark on the strip passes a fixed point at the inspection station, waits for a signal and upon receiving the signal immediately looks for a repeating mark on the strip and if no repeating mark is observed immediately stops the test and obtains an indication as to the defective roll.

* * * * *